United States Patent [19]

Drucker

[11] Patent Number: 4,895,721
[45] Date of Patent: Jan. 23, 1990

[54] PEROXIDE GEL DENTIFRICE COMPOSITIONS

[75] Inventor: Jacob Drucker, Holmdel, N.J.

[73] Assignee: Carter-Wallace Inc., New York, N.Y.

[21] Appl. No.: 146,902

[22] Filed: Jan. 22, 1988

[51] Int. Cl.$^4$ .................... A61K 7/20; A61K 33/40
[52] U.S. Cl. ........................ 424/53; 424/616
[58] Field of Search ................ 424/53, 130, 616

[56] References Cited

U.S. PATENT DOCUMENTS

| | | | |
|---|---|---|---|
| 3,639,574 | 2/1972 | Scmolka | 424/130 |
| 4,129,517 | 12/1978 | Eggensperger et al. | 424/130 |
| 4,226,851 | 10/1980 | Sompayrac | 424/53 |
| 4,431,631 | 2/1984 | Clipper et al. | 424/53 |
| 4,518,585 | 5/1985 | Greene et al. | 424/130 |
| 4,528,180 | 7/1985 | Schaeffer | 424/52 |
| 4,537,778 | 8/1985 | Clipper et al. | 424/53 |
| 4,557,935 | 12/1985 | Ekenstam et al. | 424/130 |
| 4,684,517 | 8/1987 | Clipper et al. | 424/52 |
| 4,687,663 | 8/1987 | Schaeffer | 424/52 |
| 4,781,923 | 11/1988 | Pellico | 424/130 |

*Primary Examiner*—Shep K. Rose
*Attorney, Agent, or Firm*—Kevin B. Clarke

[57] ABSTRACT

Stable aqueous peroxide dentifrice gel compositions which are stable against both viscosity and peroxide loss and which contain up to about 15% by weight of aqueous peroxide, and from about 35% to about 95% by weight of a polyol or a mixture of polyols, from about 0.75% to about 5.0% by weight of a gelling agent and from about 0.05% to about 1.0% by weight of stabilizers are disclosed.

5 Claims, No Drawings

PEROXIDE GEL DENTIFRICE COMPOSITIONS

BACKGROUND OF THE INVENTION

This invention relates to aqueous peroxide gel dentifrice compositions which are stable with respect to both peroxide level and viscosity. Said compositions comprising an aqueous peroxide, a polyol or mixtures of polyols, a gelling agent and a stabilizer. More particularly, the invention relates to dentifrice gels including aqueous hydrogen peroxide which are viscosity stable and resistant to loss of available oxygen.

Aqueous hydrogen peroxide is a well-known antiseptic material which has been widely used in the topical treatment of infectious processes. In addition, aqueous hydrogen peroxide has also been found to be useful in mouthwashes, dentifrices and oral prophylaxis generally.

Periodontists are in general agreement that substantively placing oxygen on the gums via peroxide compounds has salutary effects with respect to periodontal disorders such as gingivitis.

The rationale for this treatment is that the disorders are believed to be caused by infectious anaerobic microorganisms which are active in the absence of oxygen. The anaerobic microorganisms can be controlled or eliminated entirely by the application of compounds containing active oxygen or peroxy compounds which will readily release oxygen. The presence of oxygen creates an aerobic atmosphere which is antagonistic to the anaerobic microorganisms.

Dentifrices, especially toothpastes and powder containing active oxygen or hydrogen peroxide liberating ingredients such as peroxides, percarbonates and perborates of the alkali and alkaline earth metals or complex compounds containing hydrogen peroxide with salts of the alkali or alkaline earth metals have been known and used for some time. However, the products previously available have been found to suffer from several serious drawbacks. Principal among which is the tendency of these products to decompose within a relatively short period of time following manufacture with concomitant loss of all or a substantial amount of the available oxygen. The peroxy compounds are notoriously unstable with respect to maintenance of peroxide level as well as viscosity and have been found to be difficult to formulate into aqueous solutions or pastes which will have an adequate shelf-life and yet will readily liberate oxygen when applied to the oral cavity. Therefore, prior to the present invention, oxygen liberating compositions for the treatment of periodontal disorders or conditions have usually been formulated as anhydrous powders or water-free pastes, ointments, etc., which must be protected against contamination and chemical interaction. Additionally, these formulations have been found to be difficult or inconvenient to use since chemically reactive components are usually packaged separately and dosage cannot be easily regulated.

It has also been proposed to employ hydrogen peroxide solutions in the prophylaxis and therapy of periodontal disorders and conditions. However, these solutions have been found to be too fluid to permit effective massaging of the solution on the infected areas of the gingiva. Further, presently available hydrogen peroxide solutions, due to their extreme evanescent qualities tend to provide no more than transient aerobic conditions in the oral cavity.

In addition, considerable attempts have been made previously to provide stable peroxide gels having a concentration of up to about 15% by weight hydrogen peroxide such as disclosed in U.S. Pat. No. 3,639,574. These gel systems have been generally used in hair bleaching and the treatment of cuts and are not suggested for use in dentifrice and oral prophylaxis compositions.

SUMMARY OF THE INVENTION

In accordance with the present invention, a dentifrice or oral prophylaxis gel having a peroxide gel structure, stable with respect to the maintenance of both peroxide level and viscosity, is obtained by combining an aqueous peroxide compound, a gelling agent, a polyol and a peroxide stabilizer. The gel structures of the present invention do not require the presence of a neutralizing agent in order to provide a non-relaxing gel which maintains its viscosity and peroxide stability for periods in excess of one year at temperatures of from about 4° to about 40° C.

The foregoing dentifrice or oral prophylaxis gel compositions are provided in combination with carriers, cleaning agents, polishing agents, foaming agents, binders, humectants, flavoring materials, sweetening agents and other constituents ordinarily provided in dentifrice compositions.

The gel structure of the present invention contains up to about 15% by weight of aqueous peroxide compound from about 35% to about 95% by weight of a polyol or mixture of polyols, from about 0.75% to about 5% by weight of a gelling agent and from about 0.05% to about 1% by weight of an antioxidant.

Examples of the polyols useful in the preparation of the Peroxide gels of the present invention are those having a chain length of 3–1000 ethylene oxide units and 2 or more hydroxyl groups such as glycerine, propylene glycol, sorbitol, mannitol, polyethylene glycols, and the like having an average molecular weight of from about 200 to 7500, preferably 200 to 650.

The gelling agents employed may be the well-known carboxy vinyl polymers of extremely high molecular weight sold under the trade name Carbopol by the B. F. Goodrich Chemical Company as well as carboxypolymethylene polymers which comprise a major portion of one or more alpha, beta-olifinically unsaturated carboxylic acids, and a minor portion of a polyalkenyl polyether or a polyol, i.e., a copolymer of acrylic acid cross-linked with from about 0.75% to 1.5% of polyally; sucrose. Other specific carboxypolymethylene polymers useful herein are well-known in the art being described in U.S. Pat. Nos. 2,798,053; 2,858,281; 2,923,692; 2,985,625, and 3,657,413 which are specifically incorporated herein by reference.

The peroxide stabilizer is an antioxidant or U.V. absorbing stabilizer material is employed in the compositions of the present invention in amounts of from about 0.05% to 1.0% by weight and is a material such as butylated hydroxyanisole, butylated hydroxytoluene, propyl gallate, sodium 2,2'-dihyrdoxy-4,4'-dimethoxy-5-sulphobenzophene other substituted benzophenones of similar chemical structure or an amine oxide such as lauryl dibutylamine oxide. The stabilizer used in the peroxide solution must be toxicologically acceptable for use in dentifrice compositions.

The aqueous peroxide solutions employed in the preparation of the gels of the present invention may be obtained from any available commercial source. They may be derived from electrolytic or chemical processes. The peroxide solutions should only be prepared using deionized or otherwise purified water in order to avoid contamination or degradation of the peroxide.

The pH of the dentifrice gels of the present invention range from about 3.5 to 4.5 without neutralization by an alkaline ingredient. While neutralizing is not required in order to achieve gel and/or peroxide sability, it may be desirable to adjust the pH of the gel. The gels of the present invention may be neutralized with a compatible base such as sodium hydroxide, triethanolamine, lauryl dimethylamine oxide or tetra sodium pyrophosphate. The gel pH may be suitably adjusted to a range of from 3.5 to 6.5, preferably from 5 to 6.

The stable dentifrice gels of the present invention are Prepared by slurrying the gelling agent with the polyol or mixture of polyols and thereafter stirring for an appropriate length of time, on the order of thirty minutes or so, the mixture will swell to a thick-gel consistency, at which time the antioxidant, or U.V. absorbent material, and other constituents of the dentifrice composition are incorporated. The addition of the stabilizer is required in order to retain the peroxide level of the gel for extended periods of time after the addition of the requisite level of peroxide which follows the addition of the peroxide stabilizer and other ingredients by slow addition to the gel mass. The compositions of the present invention prepared in the aforesaid manner have been stored at environmental temperatures of up to 40° C. for more than one year and exhibited peroxide degradation of less than 0.1% per month in vitro.

Surprisingly, without the addition of the stabilizer, an apparently peroxide-free gel is formed within three months storage at environmental temperatures. While this phenomenon is not fully understood, it is believed that an inert complex may be formed by the peroxide with the polyols. No evidence of violent perxide degradation is noted under these circumstances, and a viscous gel remains indefinitely.

The gels prepared in accordance with the present invention have a viscosity of from 20,000 to about 750,000 centiposes as measured on a Brookfield viscometer.

DETAILED DESCRIPTION OF THE INVENTION

In the preparation of the novel stable dentifrice or Prophylaxis gels of the present invention, a gellant, such as a copolymer of acrylic acid cross-linked with from about 0.2% to about 2.0% of polyallylsucrose, in an amount of from about 0.75% to about 5.0% by weight, preferably approximately 2.5% by weight is slurried with a polyol or mixture of polyols, such as glycerol, sorbitol, mannitol, propylene glycol or polyethylene glycol, i.e., polymers of ethylene oxide of the general formula $HOCH_2(CH_2OCH_2)_nCHOH$ wherein n represents the average number of oxyethylene groups and has a value of from about 3 to about 1000 inclusive. The preferred polyols have a molecular weights, i.e., up to about 7500 may be employed for adjusting the viscosity characteristics of the formulation. The polyols are employed in an amount ranging from about 35% to about 95% by weight, preferably at a level of from about 40% to about 60% by weight to obtain a fluid viscosity of from 50 to 2000 centiposes at 21° C.

The slurry is vigorously agitated to obtain complete dispersion of the gellant, i.e., on the order to 20 to 40 minutes. The slurry swells to a thick gel-like consistency at which time, a peroxide stabilizer that is an antioxidant or U.V. absorber or mixtures thereof such as butylated hydroxyanisole, butylated hydroxytoluene, propyl gallate, phenocitic, sodium 2.2'-dihydroxy-4,4'-dimethoxy-5-sulphobenzophene or substituted benzophenones of similar structure or amine oxides such as lauryl dimethyl amine oxide, is incorporated in an amount of from about 0.001% to about 1.0% by weight, preferably about 0.02% to about 0.8% by weight.

After addition of the stabilizer is completed, the aqueous Peroxide solution is slowly added to the stirring gel-mass until it is thoroughly incorporated therein.

The gels so prepared have a viscosity of from about 20,000 to 750,000 centiposes as measured with the Brookfield viscometer, Model LVT, with a TF helipath spindle, 1" immersion at 0.6 rpm.

Typical examples of compositions prepared within the scope of this invention are described below; in each example as well as in the preceeding description, all parts and percentages are by weight.

EXAMPLE I 680 grams of sorbitol is placed in a suitable vessel equipped with a variable speed propeller-type stirrer and brisk mixing commenced. To the vortex created by the stirrer is carefully added 200 grams of Carbopol 940 avoiding excessive balling or lumping. The brisk mixing in continued until for at least 20 minutes or until the carboxyvinyl polymer is completely wet-out, with no lumps evident. The solvent sorbitol solution will slowly build in viscosity to a gel having a viscosity ranging from 400,000 to 800,000 cps, as the gelation starts, 2.5 grams of butylated hydroxyanisole is incorporated into the gel followed by a careful addition of 290.5 grams of aqueous hydrogen peroxide solution over a period of about 30 seconds. The stirrer speed is lowered as the viscosity of the batch decreases from 200,000 to 400,000 cps. The mixing is continued for a minimum of about 15 minutes until a uniform blend is achieved. The pH of the resultant blend ranges from 4 to 5.

It was desired to increase the pH of the blend to approximately 5.3 thus 5 grams of triethanolamine was added slowly over a period of approximately 60 seconds.

Th viscosity of the blend, when stabilized after 24 hours, was determined to be 450,000 cps at 21° C.

EXAMPLE II

Following the procedure of Example I, a gel suitable for use as a dentifrice was prepared containing the following ingredients:

|  | W/W |
|---|---|
| *Carbopol 940 | 1.50 |
| +Polyethylene Glycol 400 | 30.00 |
| Glycerine 99.6% | 25.00 |
| Butylated Hydroxy Anisole | 0.50 |
| Hydrogen Peroxide (35% sol.) | 10.00 |
| Sodium Saccharin | 0.50 |
| Mixed Flavor Oils | 1.00 |
| Calcium Pyrophosphate | 29.00 |
| Sodium Lauryl Sarcosinate | 1.50 |
| Tetrasodium Pyrophosphate | 1.00 |

* A copolymer of acrylic acid and polyallyl sucrose having an average of 5.8 allyl groups per sucrose molecule.
+ A polyethylene glycol polymer having an average of 400 oxyethylene groups.

Table I, which follows, indicates the results of peroxide content and viscosity tests performed on the dentifrice gels of the present invention after periods of storage in glass jars are various temperatures.

The procedure followed to determine peroxide content was as follows:

A 1.0 gram sample of the dentifrice gel obtained following Example II was placed in a 250 ml. beaker and 100 ml. of a 0.5N HCl solution was added and the mixture stirred until the gel was sufficiently broken down and dispersed. A surfactant such as sodium lauryl sulfate may be used to facilitate the dispersion. The beaker was then placed in a magnetic stirring platform and several drops of a 3% solution of ammonium molybdate were added, then approximately 1.0 gram of potassium iodide and the mixture stirred to allow complete dissolution of crystals present.

The iodine released by the reaction of acidified peroxide and potassium iodide was titrated with a 0.1N sodium thiosulfate solution until the solution becomes slightly yellow, a stabilized starch indicator solution is added in an amount sufficient to give a blue color to solution, then the solution is titrated until the blue color disappears. Record the volume in ml. of titrant required to react with the iodine.

The calculation of peroxide content was made according to the following equation:

$$\% H_2O_2 = \frac{\text{Volume of sodium thiosulfate sol.}}{\text{Weight of sample}} \times \text{normality of Nathiox 1.7}$$

The viscosity of the samples was measured at the temperatures indicated in Table 2 with a Brookfield viscometer, Model LVT, with a TF helipath spindle, at 1 inch immersion, at 0.6 rpm 60 second - 90 second reading.

TABLE 1

| Peroxide Level % | | | | | |
|---|---|---|---|---|---|
| Temperature | 4° C. | 21° C. | 30° C. | 37° C. | 40° C. |
| Initial $H_2O_2$ Content | 10.00 | 10.00 | 10.00 | 10.00 | 10.00 |
| $H_2O_2$ after 1 year | 9.50 | 8.92 | 8.50 | 7.50 | 7.50 |

TABLE 2

Viscosity 60 sec./90 sec.
Determined on Brookfield Model LVT - using Helipath TF spindles and attached at 0.6 rpm. Values given are scale readings.

| Temperature | 4° C. | 21° C. | 28° C. | 37° C. | 40° C. |
|---|---|---|---|---|---|
| Initial | 40/53 | 42/48 | 36/42 | 34/48 | 35/45 |
| 1 Month | 41/55 | 37/45 | 35/42 | 35/45 | 36/44 |
| 6 Months | 42/50 | 38/48 | 36/44 | 36/46 | 38/46 |
| 1 Year | 44/50 | 40/50 | 38/46 | 46/48 | 48/50 |

It will be noted that the foregoing is illustrative only of the present invention and that obvious modifications will occur to those skilled in the arts and fall within the scope of the appended claims.

What is claimed is:

1. Stable, aqueous, non-relaxing peroxide gel compositions consisting essentially of from about 35% to about 95% by weight of a complexing agent selected from the group consisting of ethylene polymers of the formula $HOCH_2(CH_2OCH_2)_nCHOH$ wherein n has a value of 3 to 1000 and mixtures thereof, from about 0.75% to about 5.00% by weight of a gelling agent selected from the group consisting of carboxypolymethylene polymers comprising a major portion of an alpha, beta-olefinically unsaturated carboxylic acid and a minor portion of a polyalkenyl polyether or a polyol and carboxy vinyl polymers, from about 0.05% to about 1.00% by weight of a peroxide stabilizer selected from the group comprising butylated hydroxyanisole, butylated hydroxy toluene, propyl gallate, sodium 2,2'-dihydroxy-4,4'-dimethoxy-5-sulphobenzone, lauryl dibutylamine oxide and the like and up to about 15.00% by weight of hydrogen peroxide.

2. Aqueous peroxide gels as claimed in claim 1 wherein said complexing agents have molecular weights of from about 200 to about 7500.

3. Aqueous peroxide gels as claimed in claim 2 wherein said complexing agents are selected from the group comprising glycerol, sorbitol, mannitol, propylene glycol and polyalkylene glycols.

4. Aqeous peroxide gels as claimed in claim 1 wherein said gelling agent is a copolymer of acrylic acid crosslinked with from about 0.75% to about 1.5% by weight, based on the weight of acrylic, of polyallyl sucrose.

5. A dentifrice composition consisting essentially of about 1.50% by weight of a copolymer of acrylic acid and polyallylosucrose having an average of about 8.8 allyl groups per sucrose molecule, about 30.00% by weight of a polyethylene glycol polymer having an average of about 400 oxyethylene groups, about 25.00% by weight glycerine, about 0.50% by weight butylated hydroxy anisole, about 10.00% by weight hydrogen peroxide in a 35.00% by weight aqueous hydrogen peroxide solution, about 0.50% by weight sodium saccharin, about 29.00% by weight calcium pyrophosphate, about 1.50% by weight sodium lauryl sarcosinate, about 1.50% by weight tetrasodium pyrophosphate and about 1.00% by weight flavor.

* * * * *